(12) United States Patent
Cruanes et al.

(10) Patent No.: US 10,795,914 B2
(45) Date of Patent: **\*Oct. 6, 2020**

(54) QUERY PLANS FOR ANALYTIC SQL CONSTRUCTS

(71) Applicant: Snowflake Inc., San Mateo, CA (US)

(72) Inventors: Thierry Cruanes, San Mateo, CA (US); Benoit Dageville, Foster City, CA (US); Allison Waingold Lee, San Carlos, CA (US)

(73) Assignee: Snowflake Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,458

(22) Filed: Apr. 29, 2020

(65) Prior Publication Data

US 2020/0278983 A1 Sep. 3, 2020

Related U.S. Application Data

(63) Continuation of application No. 16/741,676, filed on Jan. 13, 2020, which is a continuation of application
(Continued)

(51) Int. Cl.
| | | |
|---|---|---|
| *G06F 15/16* | (2006.01) | |
| *G06F 16/27* | (2019.01) | |
| *G06F 9/50* | (2006.01) | |
| *H04L 29/08* | (2006.01) | |
| *G06F 9/48* | (2006.01) | |
| *G06F 16/2455* | (2019.01) | |
| *G06F 16/2453* | (2019.01) | |
| *G06F 16/9535* | (2019.01) | |
| *G06F 16/2458* | (2019.01) | |
| *G06F 16/23* | (2019.01) | |
| *G06F 16/182* | (2019.01) | |

(Continued)

(52) U.S. Cl.
CPC ............ *G06F 16/27* (2019.01); *G06F 9/4881* (2013.01); *G06F 9/5016* (2013.01); *G06F 9/5044* (2013.01); *G06F 9/5083* (2013.01); *G06F 9/5088* (2013.01); *G06F 16/148* (2019.01); *G06F 16/1827* (2019.01); *G06F 16/211* (2019.01); *G06F 16/221* (2019.01); *G06F 16/2365* (2019.01); *G06F 16/2456* (2019.01); *G06F 16/2471* (2019.01); *G06F 16/24532* (2019.01); *G06F 16/24545* (2019.01); *G06F 16/24552* (2019.01); *G06F 16/951* (2019.01); *G06F 16/9535* (2019.01); *H04L 67/1095* (2013.01); *H04L 67/1097* (2013.01); *H04L 67/2842* (2013.01)

(58) Field of Classification Search
None
See application file for complete search history.

(56) References Cited

U.S. PATENT DOCUMENTS

2010/0332472 A1\* 12/2010 Graefe .............. G06F 16/24542
707/736
2011/0131199 A1 6/2011 Simon et al.
(Continued)

*Primary Examiner* — Alex Gofman
(74) *Attorney, Agent, or Firm* — Womble Bond Dickinson (US) LLP; Daniel E. Ovanezian

(57) ABSTRACT

A system and method for managing data storage and data access with querying data in a distributed system without buffering the results on intermediate operations in disk storage.

30 Claims, 8 Drawing Sheets

Related U.S. Application Data

No. 14/626,853, filed on Feb. 19, 2015, now Pat. No. 10,534,792.

(60) Provisional application No. 61/941,986, filed on Feb. 19, 2014.

(51) Int. Cl.
*G06F 16/951* (2019.01)
*G06F 16/22* (2019.01)
*G06F 16/21* (2019.01)
*G06F 16/14* (2019.01)

(56) References Cited

U.S. PATENT DOCUMENTS

| | | |
|---|---|---|
| 2011/0191324 A1 | 8/2011 | Wang et al. |
| 2013/0066855 A1* | 3/2013 | Gupta .................. G06F 16/951 707/722 |
| 2013/0262433 A1 | 10/2013 | Qiu et al. |
| 2014/0372365 A1 | 12/2014 | Weyerhaeuser et al. |

\* cited by examiner

QUERY PLANS FOR ANALYTIC SQL CONSTRUCTS

CROSS REFERENCE TO RELATED APPLICATIONS

This application is a continuation of U.S. patent application Ser. No. 16/741,676, filed Jan. 13, 2020, entitled "Query Plans for Analytic SOL Constructs," which is a continuation of U.S. patent application Ser. No. 14/626,853, filed Feb. 19, 2015, entitled "Query Plans for Analytic SQL Constructs," issued as U.S. Pat. No. 10,534,792 on Jan. 14, 2020, which claims benefit of U.S. Provisional Application Ser. No. 61/941,986, entitled "Apparatus and method for enterprise data warehouse data processing on cloud infrastructure," filed Feb. 19, 2014, the disclosure of which is incorporated herein by reference in its entirety.

TECHNICAL FIELD

The present disclosure relates to resource management systems and methods that manage data storage and computing resources.

BACKGROUND

Many existing data storage and retrieval systems are available today. For example, in a shared-disk system, all data is stored on a shared storage device that is accessible from all of the processing nodes in a data cluster. In this type of system, all data changes are written to the shared storage device to ensure that all processing nodes in the data cluster access a consistent version of the data. As the number of processing nodes increases in a shared-disk system, the shared storage device (and the communication links between the processing nodes and the shared storage device) becomes a bottleneck that slows data read and data write operations. This bottleneck is further aggravated with the addition of more processing nodes. Thus, existing shared-disk systems have limited scalability due to this bottleneck problem.

Another existing data storage and retrieval system is referred to as a "shared-nothing architecture." In this architecture, data is distributed across multiple processing nodes such that each node stores a subset of the data in the entire database. When a new processing node is added or removed, the shared-nothing architecture must rearrange data across the multiple processing nodes. This rearrangement of data can be time-consuming and disruptive to data read and write operations executed during the data rearrangement. Further, this architecture requires at least one processing node to store data. Thus, the shared-nothing architecture fails to store data if all processing nodes are removed. Additionally, management of data in a shared-nothing architecture is complex due to the distribution of data across many different processing nodes.

The systems and methods described herein provide an improved approach to data storage and data retrieval that alleviates the above-identified limitations of existing systems.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1A:
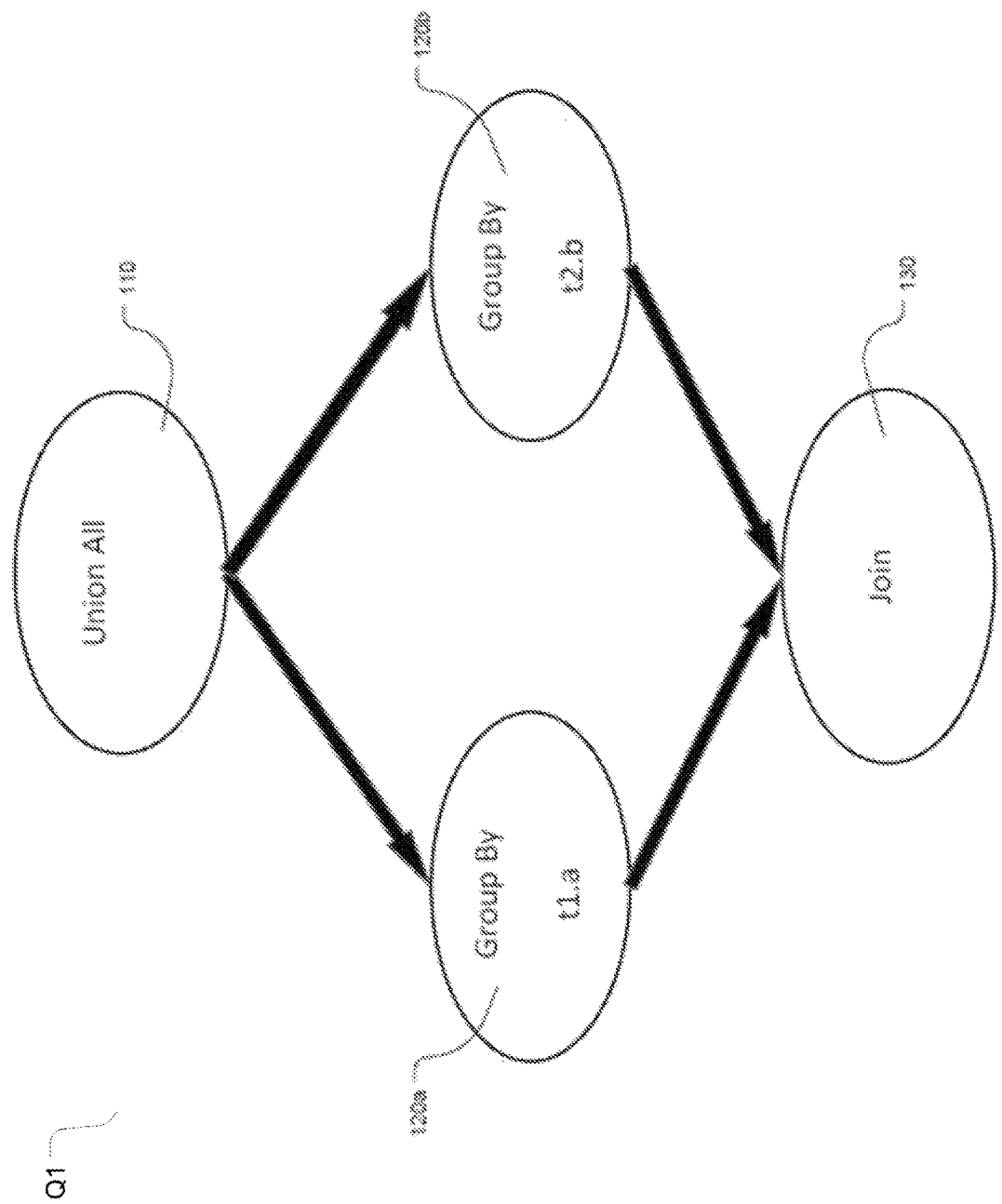
FIG. 1A illustrates an information flow diagram depicting a join process within a distributed system.

Disclosed herein are systems, apparatuses and methods for managing data storage and data access for querying data in a distributed system without buffering intermediate results to disk storage during use. For example, an implementation may comprise an access module configured for accessing a query plan having a plurality of operators, wherein a first operator in the query plan processes a set of data to generate a first result. Additionally, after first operator has begun to produce an output the output is pushed to a plurality of secondary operators to generate a second result from the output. In the disclosed systems, because a subsequent operator is enabled by the disclosed methods to begin working on any amount of output as it is produced from a preceding operator, the buffering needed between operators may be greatly reduced or eliminated.

In the following description, reference is made to the accompanying drawings that form a part thereof, and in which is shown by way of illustration specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

Reference throughout this specification to "one embodiment," "an embodiment," "one example" or "an example" means that a particular feature, structure or characteristic described in connection with the embodiment or example is included in at least one embodiment of the present disclosure. Thus, appearances of the phrases "in one embodiment," "in an embodiment," "one example" or "an example" in various places throughout this specification are not necessarily all referring to the same embodiment or example. Furthermore, the particular features, structures, databases or characteristics may be combined in any suitable combinations and/or sub-combinations in one or more embodiments or examples. In addition, it should be appreciated that the figures provided herewith are for explanation purposes to persons ordinarily skilled in the art and that the drawings are not necessarily drawn to scale.

Embodiments in accordance with the present disclosure may be embodied as an apparatus, method or computer program product. Accordingly, the present disclosure may take the form of an entirely hardware-comprised embodiment, an entirely software-comprised embodiment (including firmware, resident software, micro-code, etc.) or an embodiment combining software and hardware aspects that may all generally be referred to herein as a "circuit," "module" or "system." Furthermore, embodiments of the present disclosure may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present disclosure may be written in any combination of one or more programming languages. Such code may be compiled from source code to computer-readable assembly language or machine code suitable for the device or computer on which the code will be executed.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction and then scaled accordingly. A cloud model can be composed of various characteristics (e.g., on-demand self-service, broad network access, resource pooling, rapid elasticity, and measured service), service models (e.g., Software as a Service ("SaaS"), Platform as a Service ("PaaS"), and Infrastructure as a Service ("IaaS")), and deployment models (e.g., private cloud, community cloud, public cloud, and hybrid cloud).

The flow diagrams and block diagrams in the attached figures illustrate the architecture, functionality, and operation of possible implementations of systems, methods, and computer program products according to various embodiments of the present disclosure. In this regard, each block in the flow diagrams or block diagrams may represent a module, segment, or portion of code, which comprises one or more executable instructions for implementing the specified logical function(s). It will also be noted that each block of the block diagrams and/or flow diagrams, and combinations of blocks in the block diagrams and/or flow diagrams, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow diagram and/or block diagram block or blocks.

The systems and methods described herein provide a flexible and scalable data warehouse using a new data processing platform. In some embodiments, the described systems and methods leverage a cloud infrastructure that supports cloud-based storage resources, computing resources, and the like. Example cloud-based storage resources offer significant storage capacity available on-demand at a low cost. Further, these cloud-based storage resources may be fault-tolerant and highly scalable, which can be costly to achieve in private data storage systems. Example cloud-based computing resources are available on-demand and may be priced based on actual usage levels of the resources. Typically, the cloud infrastructure is dynamically deployed, reconfigured, and decommissioned in a rapid manner.

In the described systems and methods, a data storage system utilizes an SQL (Structured Query Language)-based relational database. However, the systems and methods disclosed herein are applicable to any type of database using any data storage architecture and using any language to store and retrieve data within the database. Additionally, the systems and methods described herein further provide a multi-tenant system that supports isolation of computing resources and data between different customers/clients and between different users within the same customer/client.

A relational join is one of the fundamental data processing operations in a relational data management system. A join is a binary operator, taking two relations R and S, and a binary predicate $\theta$ as inputs, and producing a single relation $R[?]_\theta$ S which contains the set of all combinations of tuples in R and S which satisfy the predicate $\theta$.

A single query typically performs multiple such join operations, resulting in a tree-shaped execution plan. Join operations form intermediate nodes and group nodes of that tree shape, while base relations form analogous leaves of that tree. Data flows from the leaves of the tree towards the root, where the final query result is produced. The execution time of a query is directly related to the amount of intermediate data it produces. Relational data management systems thus seek to minimize the amount of intermediate data which flows through the tree in order to minimize the execution time of the query.

This disclosure discloses a method for pushing results of primary operators to an operator further down the tree, without having to buffer the results. Such methods are advantageous in SQL constructs. There are several SQL constructs which are frequently used in analytics queries, which rely on scanning an intermediate result many times in order to compute a result. These may include: grouping sets, rollup, and cube aggregates. These SQL constructs allow aggregations along multiple dimensions of a data set to be generated into a single result set. Other SQL constructs, referred to as "window aggregates" allow aggregates across different partitions of a dataset to be produced into a single result set. In another SQL construct, distinct aggregates compute an aggregate function on an expression, ignoring duplicate values of the expression because multiple distinct aggregates require eliminating duplicates along different attributes of the same intermediate data set.

The intermediate result that is input to these forms of aggregation can be a base table, or the result of earlier processing, e.g. filters, joins, aggregations, etc., which could be arbitrarily complex.

Current database systems evaluate such queries in one of two ways: The input relation is recomputed for each step of the plan that consumes the input. This can be undesirable if the input relation is the result of expensive operations. This technique is referred to as "inlining" of the input relation. The query may also be evaluated in two steps. The first step evaluates the input relation and materializes its result to a temporary structure that is typically stored and/or buffered in memory, or written to disk if the input relation is too large for memory. The second step evaluates the aggregation, with each consumer of the input relation reading from the temporary structure. The resource cost of materializing and reading back the input relation can be large, e.g. if the result does not fit in memory and must be written to disk, resulting in higher economic and operational costs. Also, materializing the intermediate result is a blocking operator, which breaks the pipelining of the plan. As used herein the terms "cost of materializing" and "cost of reading back" are intended to denote all of the resources, expenses, and costs associated with materializing and reading back results from various operators, both operationally and economically. This technique may be referred to as "materialization" of the input relation.

Figure 1B:
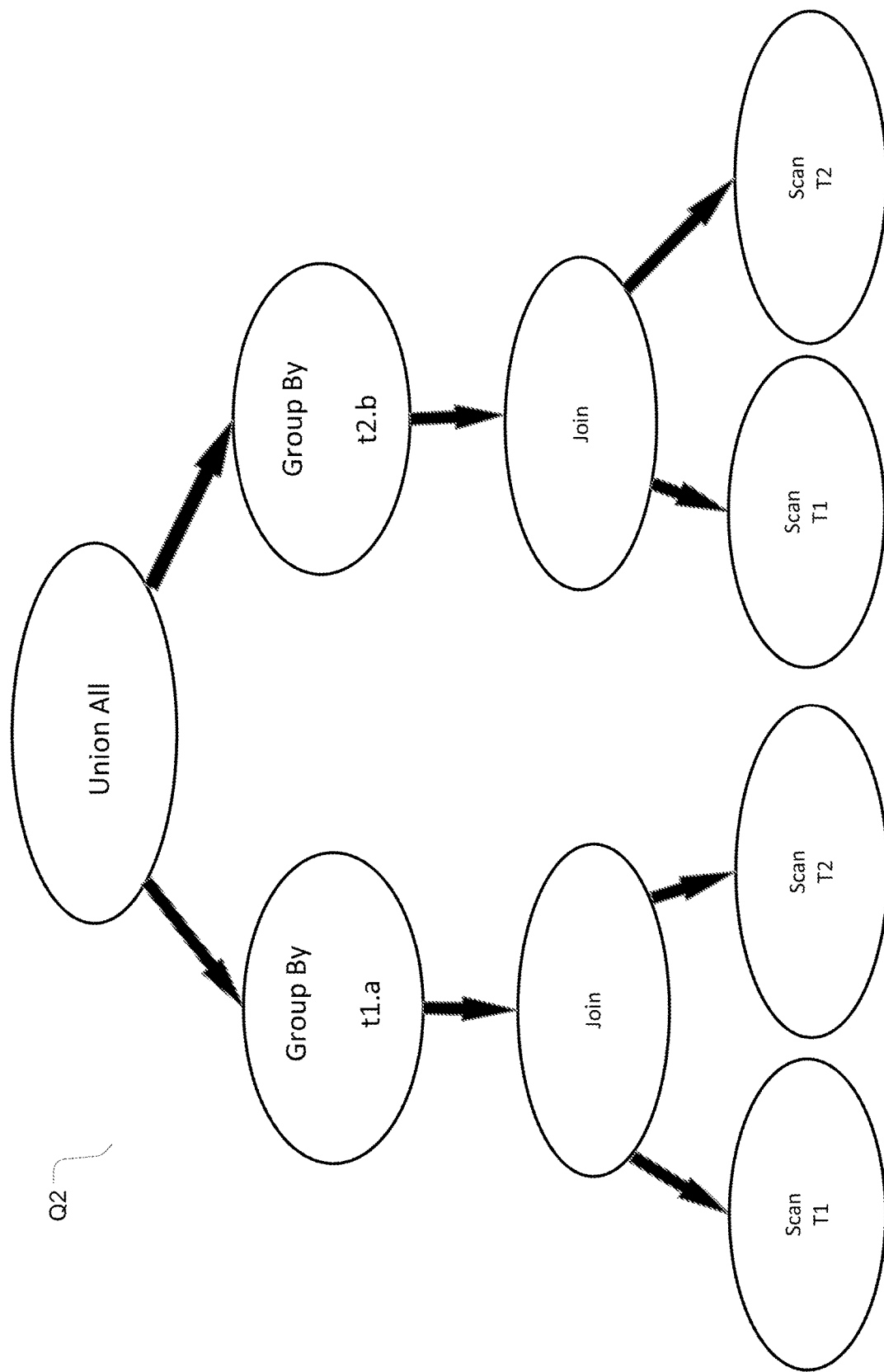
FIG. 1B illustrates an information flow diagram depicting a join process within a distributed system.
Figure 1C:
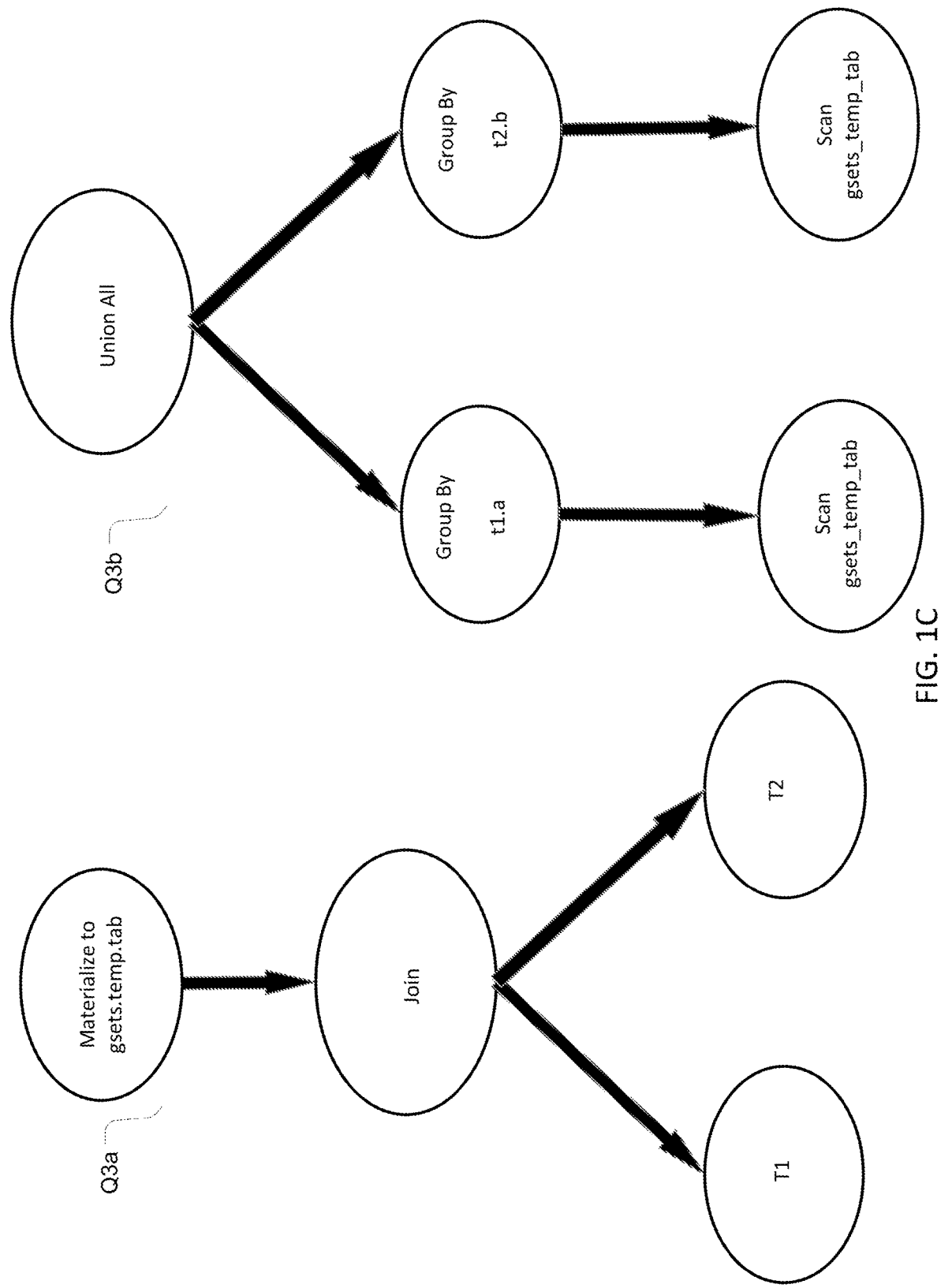
FIG. 1C illustrates an information flow diagram depicting a join process within a distributed system.

An example of a grouping sets query is illustrated as Q1 in FIG. 1A:

Q1
select t1.a, t2.b, count(*)
from t1, t2
where t1.x=t2.y
group by grouping sets (t1.a, t2.b);

Using the above in described inlining, the following equivalent query (illustrated as Q2 in FIG. 1B) would be executed:

Q2
select t1.a, null as t2.b, count(*)
from t1, t2
where t1.x=t2.y
group by t1.a
union all
select null as t1.a, t2.b, count(*)
from t1, t2
where t1.x=t2.y
group by t2.b;

Using materialization, the following equivalent sequence of queries illustrated in FIG. 1C would be executed:

Q3a
create table gsets_temp_tab as
select t1.a, t2.b
from t1, t2
where t1.x=t2.y;
select t1.a, null as t2.b, count(*)
from gsets_temp_tab
group by t1.a
Q3b
union all
select null as t1.a, t2.b, count(*)
from gsets_temp_tab
group by t2.b;
drop table gsets_temp_tab;

Most commercial database systems use a combination of the above techniques, using either heuristics or a cost-model to determine whether materialization or inlining is likely to be most efficient for a particular aggregation in a particular query. In the example above, the more optimal execution technique would depend on how costly it is to compute the join of t1 and t2, versus the cost of materializing the result, which would depend on the size of the result.

An improved execution model may use a "push model" to schedule operators in a plan. When one operator finishes processing data, it pushes its results to the operator who consumes the result, and that operator then does its work. This model allows an operator to push its result to multiple secondary operators/consumers of the same intermediate result for concurrent processing. This is advantageous for implementing SQL constructs that require processing the same data set in different ways. As used herein the phrase "unique operators" is intended to denote first, second, and n-operators that are different in form or function from other operators within a query plan or portion of a query plan.

Figure 2:
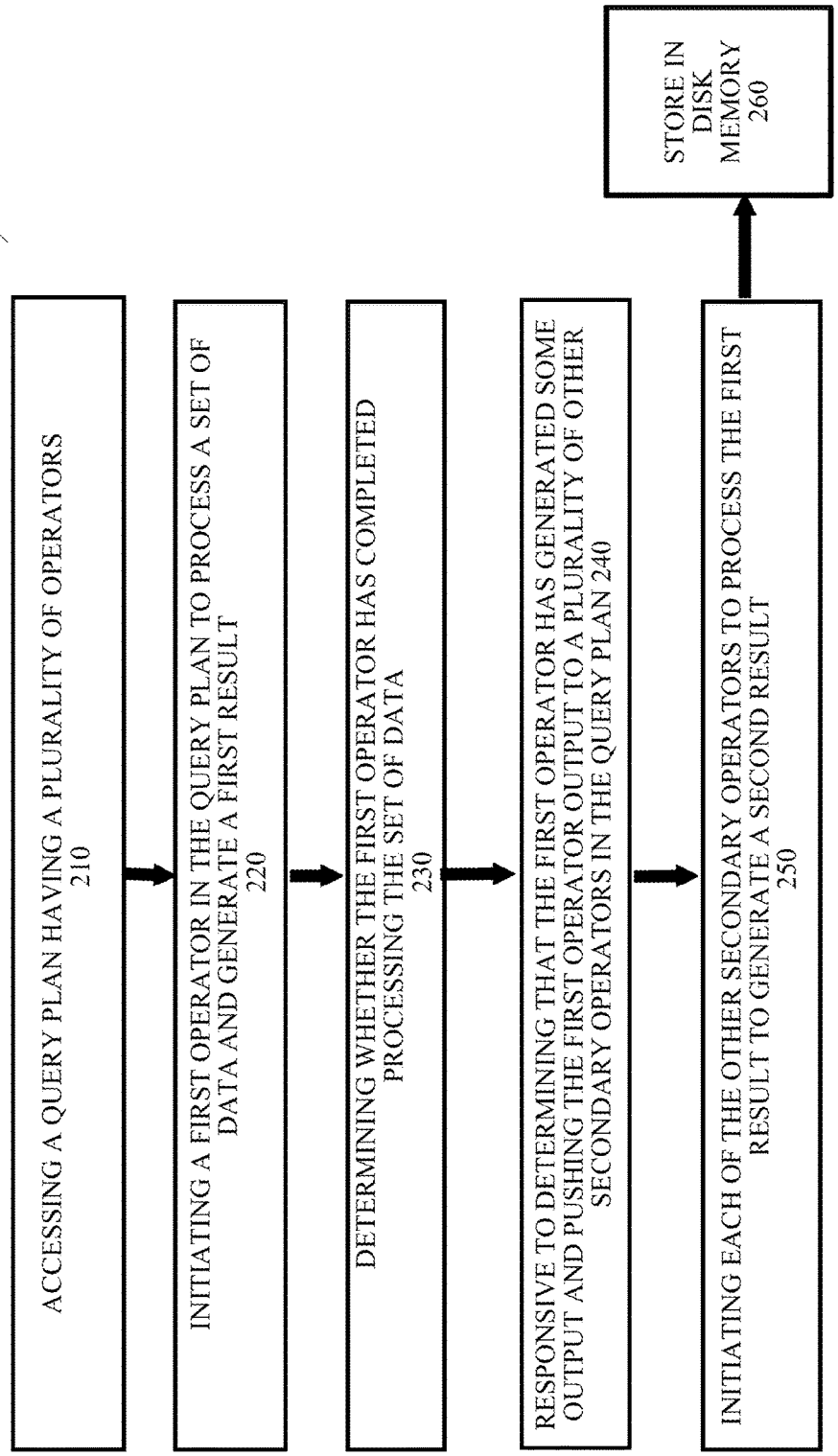
FIG. 2 is a process flow diagram depicting an implementation of the methods disclosed herein.

Further, as illustrated in FIG. 1, query Q1 processed herein using the method 200 of FIG. 2, disclosed for the execution model, the result of the join operator 110 can be directly pushed to both of the group-by nodes 120a, 120b in the expanded query (Q2) without having to buffer the results in disk storage. In this embodiment the group-by nodes 120a, 120b may be secondary or intermediate operators that may process the results of the join operator 110 with different operations. After all of the group-by nodes 120a, 120b have consumed the results, the results may be finally aggregated by a final join operation 130.

Using this kind of plan avoids both re-computing the result of the join, and the cost of materializing the result of the join. The group-by operators can execute concurrently, such that the pipeline from the join to the group-bys is not broken. Additionally, in an implementation, each of the secondary operators may be different from one another, such that the same intermediate data may be processed differently as may be required in SQL constructs.

Illustrated in FIG. 2 is a flow diagram for a method 200 of performing a join operation without the need to buffer in disk storage. At 210 of the method 200, a query plan having a plurality of operators may be accessed. It should be noted that in an implementation, each of the plurality of operators may comprise differing processes for the same result it consumes. The plurality of operators may be run concurrently and timed so that their results are coordinated properly for a final join operation.

At 220, the method 200 may call for the initiation of a first operator in the query plan to process a set of data and generate a first result. At 230 it may be determined whether the first operator has completed processing the set of data, and responsive to determining that the first operator has generated some output, pushing the first operator output to a plurality of other secondary operators in the query plan at 240.

Finally at 250, initiating each of the other secondary operators to process the first result to generate a second result that may result in a final join that may be stored on disk memory at 260.

In contrast, other commercial database systems use a pull model, which forces a decision between either the inlining or materialization methods described above.

The methods disclosed herein may be used to improve performance of analytics queries in a distributed relation system.

Figure 3:
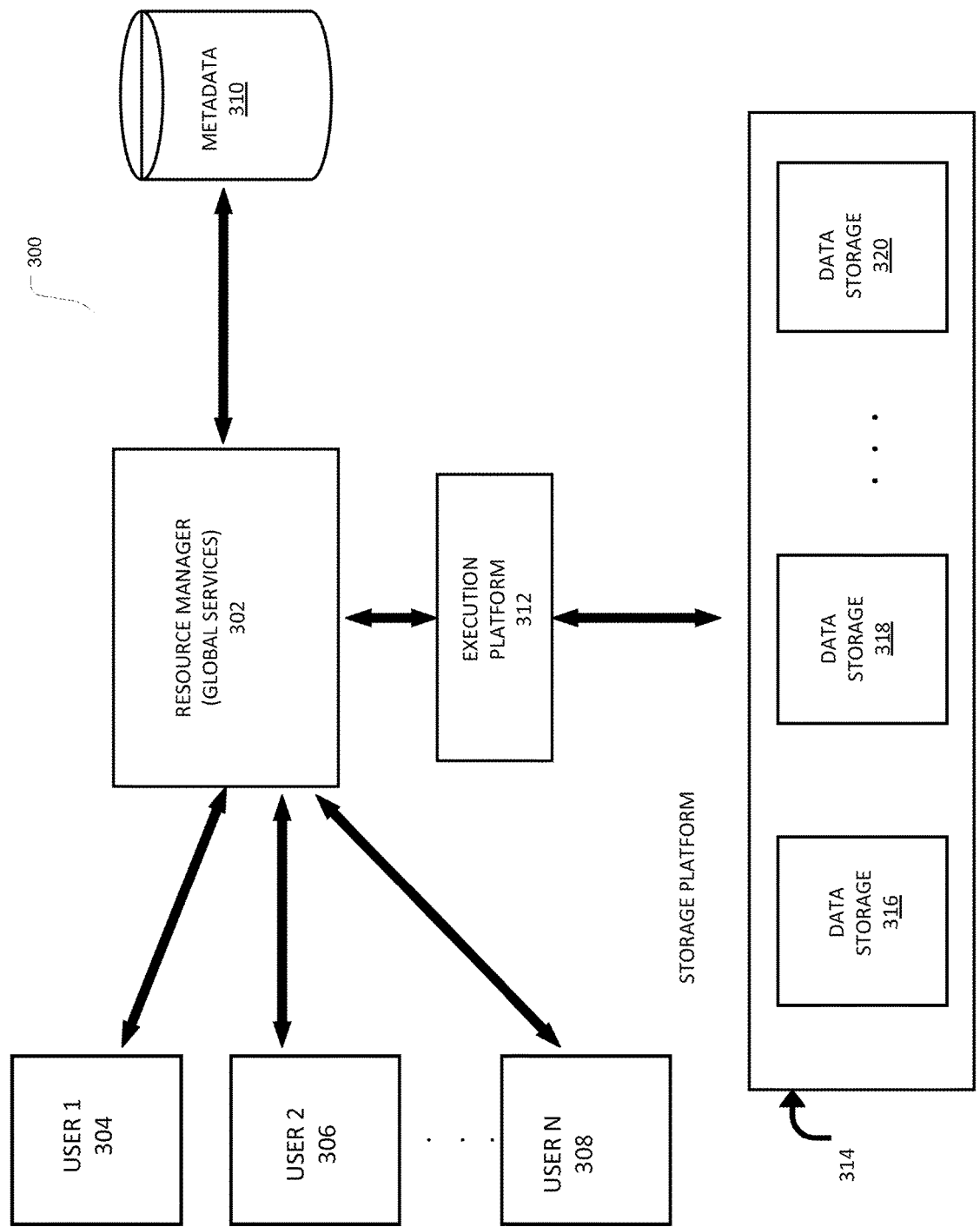
FIG. 3 illustrates a block diagram depicting an embodiment of an operating environment in accordance with the teachings of the disclosure.

Illustrated in FIG. 3 is a computer system for running the methods disclosed herein. As shown in FIG. 3, a resource manager 302 is coupled to multiple users 304, 306, and 308. In particular implementations, resource manager 302 can support any number of users desiring access to data processing platform 300. Users 304-308 may include, for example, end users providing data storage and retrieval requests, system administrators managing the systems and methods described herein, and other components/devices that interact with resource manager 302. Resource manager 302 provides various services and functions that support the operation of all systems and components within data processing platform 300. Resource manager 302 is also coupled to metadata 310, which is associated with the entirety of data stored throughout data processing platform 300. In some embodiments, metadata 310 includes a summary of data stored in remote data storage systems as well as data available from a local cache. Additionally, metadata 310 may include information regarding how data is organized in the remote data storage systems and the local caches. Metadata 310 allows systems and services to determine whether a piece of data needs to be processed without loading or accessing the actual data from a storage device.

Resource manager 302 is further coupled to an execution platform 312, which provides multiple computing resources that execute various data storage and data retrieval tasks, as discussed in greater detail below. Execution platform 312 is coupled to multiple data storage devices 316, 318, and 320 that are part of a storage platform 314. Although three data storage devices 316, 318, and 320 are shown in FIG. 3, execution platform 312 is capable of communicating with any number of data storage devices. In some embodiments, data storage devices 316, 318, and 320 are cloud-based storage devices located in one or more geographic locations. For example, data storage devices 316, 318, and 320 may be part of a public cloud infrastructure or a private cloud infrastructure. Data storage devices 316, 318, and 320 may be hard disk drives (HDDs), solid state drives (SSDs), storage clusters or any other data storage technology. Additionally, storage platform 314 may include distributed file systems (such as Hadoop Distributed File Systems (HDFS)), object storage systems, and the like.

In particular embodiments, the communication links between resource manager 302 and users 304-308, metadata 310, and execution platform 312 are implemented via one or more data communication networks. Similarly, the communication links between execution platform 312 and data storage devices 316-320 in storage platform 314 are implemented via one or more data communication networks. These data communication networks may utilize any communication protocol and any type of communication medium. In some embodiments, the data communication networks are a combination of two or more data communication networks (or sub-networks) coupled to one another. In alternate embodiments, these communication links are implemented using any type of communication medium and any communication protocol.

As shown in FIG. 3, data storage devices 316, 318, and 320 are decoupled from the computing resources associated with execution platform 312. This architecture supports dynamic changes to data processing platform 300 based on the changing data storage/retrieval needs as well as the changing needs of the users and systems accessing data processing platform 300. The support of dynamic changes allows data processing platform 300 to scale quickly in response to changing demands on the systems and components within data processing platform 300. The decoupling of the computing resources from the data storage devices supports the storage of large amounts of data without requiring a corresponding large amount of computing resources. Similarly, this decoupling of resources supports a significant increase in the computing resources utilized at a particular time without requiring a corresponding increase in the available data storage resources.

Resource manager 302, metadata 310, execution platform 312, and storage platform 314 are shown in FIG. 3 as individual components. However, each of resource manager 302, metadata 310, execution platform 312, and storage platform 314 may be implemented as a distributed system (e.g., distributed across multiple systems/platforms at multiple geographic locations). Additionally, each of resource manager 302, metadata 310, execution platform 312, and storage platform 314 can be scaled up or down (independently of one another) depending on changes to the requests received from users 304-308 and the changing needs of data processing platform 300. Thus, in the described embodiments, data processing platform 300 is dynamic and supports regular changes to meet the current data processing needs.

Figure 4:
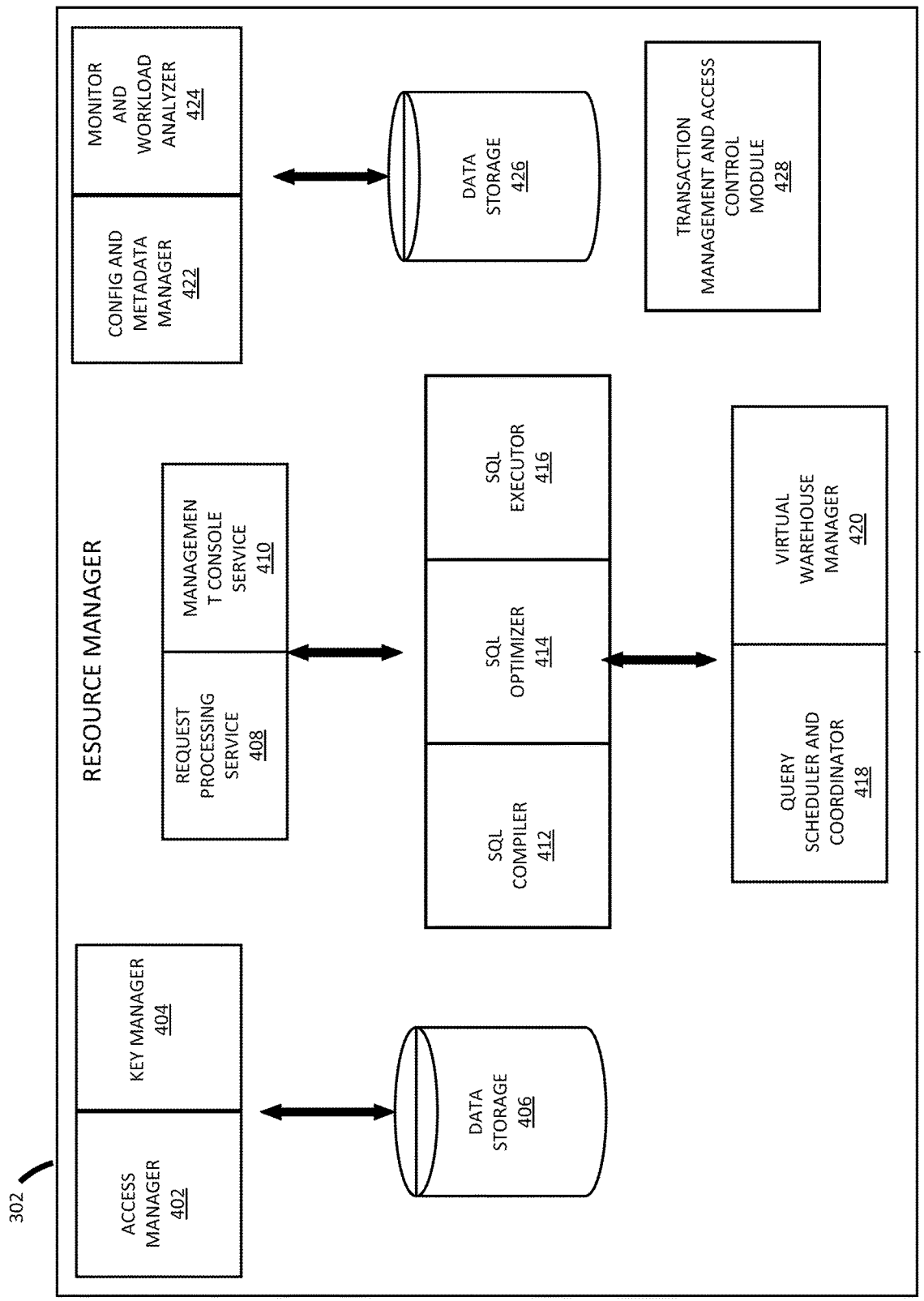
FIG. 4 illustrates a block diagram depicting an example of an implementation of a resource manager in accordance with the teachings of the disclosure.

FIG. 4 is a block diagram depicting an embodiment of resource manager 302. As shown in FIG. 3, resource manager 302 includes an access manager 402 and a key manager 404 coupled to a data storage device 406. Access manager 402 handles authentication and authorization tasks for the systems described herein. Key manager 404 manages storage and authentication of keys used during authentication and authorization tasks. A request processing service 408 manages received data storage requests and data retrieval requests. A management console service 410 supports access to various systems and processes by administrators and other system managers.

Resource manager 302 also includes an SQL compiler 412, an SQL optimizer 414 and an SQL executor 410. SQL compiler 412 parses SQL queries and generates the execution code for the queries. SQL optimizer 414 determines the best method to execute queries based on the data that needs to be processed. SQL executor 416 executes the query code for queries received by resource manager 302. A query scheduler and coordinator 418 sends received queries to the appropriate services or systems for compilation, optimization, and dispatch to an execution platform. A virtual warehouse manager 420 manages the operation of multiple virtual warehouses implemented in an execution platform.

Additionally, resource manager 302 includes a configuration and metadata manager 422, which manages the information related to the data stored in the remote data storage devices and in the local caches. A monitor and workload analyzer 424 oversees the processes performed by resource manager 302 and manages the distribution of tasks (e.g., workload) across the virtual warehouses and execution nodes in the execution platform. Configuration and metadata manager 422 and monitor and workload analyzer 424 are coupled to a data storage device 426.

Resource manager 302 also includes a transaction management and access control module 428, which manages the various tasks and other activities associated with the processing of data storage requests and data access requests. For example, transaction management and access control module 428 provides consistent and synchronized access to data by multiple users or systems. Since multiple users/systems may access the same data simultaneously, changes to the data must be synchronized to ensure that each user/system is working with the current version of the data. Transaction management and access control module 428 provides control of various data processing activities at a single, centralized location in resource manager 302.

Figure 5:
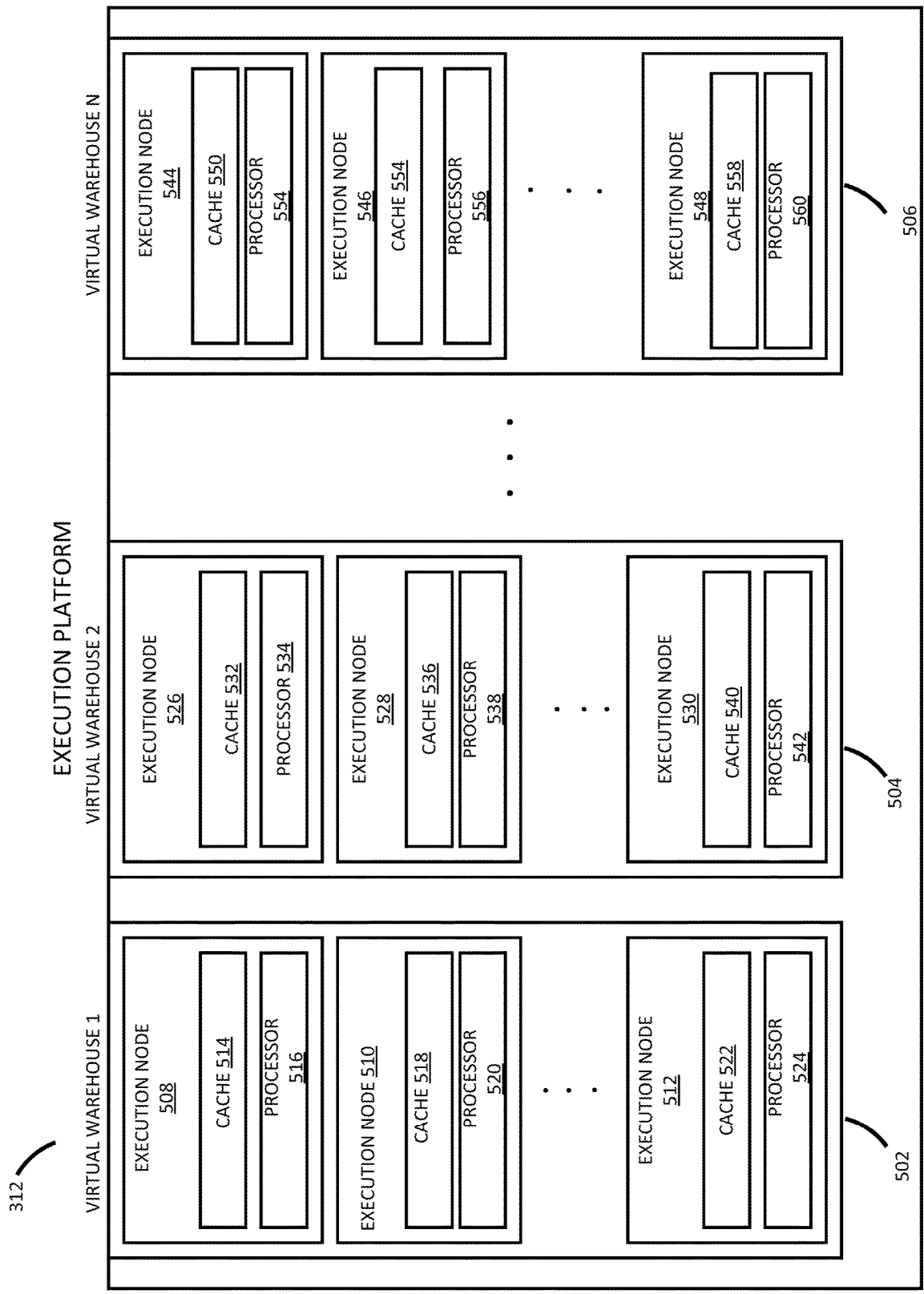
FIG. 5 illustrates a block diagram depicting an example of an implementation of a execution platform in accordance with the teachings of the disclosure.

FIG. 5 is a block diagram depicting an embodiment of an execution platform. As shown in FIG. 5, execution platform 512 includes multiple virtual warehouses 502, 504, and 506. Each virtual warehouse includes multiple execution nodes that each include a cache and a processor. Although each virtual warehouse 502-506 shown in FIG. 5 includes three execution nodes, a particular virtual warehouse may include any number of execution nodes. Further, the number of execution nodes in a virtual warehouse is dynamic, such that new execution nodes are created when additional demand is present, and existing execution nodes are deleted when they are no longer necessary.

Each virtual warehouse 502-506 is capable of accessing any of the data storage devices 316-320 shown in FIG. 3. Thus, virtual warehouses 502-506 are not necessarily assigned to a specific data storage device 316-320 and, instead, can access data from any of the data storage devices 316-320. Similarly, each of the execution nodes shown in FIG. 5 can access data from any of the data storage devices 316-320. In some embodiments, a particular virtual warehouse or a particular execution node may be temporarily assigned to a specific data storage device, but the virtual warehouse or execution node may later access data from any other data storage device.

In the example of FIG. 5, virtual warehouse 502 includes three execution nodes 508, 510, and 512. Execution node 508 includes a cache 514 and a processor 516. Execution node 510 includes a cache 518 and a processor 520. Execution node 512 includes a cache 522 and a processor 524. Each execution node 508-512 is associated with processing one or more data storage and/or data retrieval tasks. For example, a particular virtual warehouse may handle data storage and data retrieval tasks associated with a particular user or customer. In other implementations, a particular virtual warehouse may handle data storage and data retrieval tasks associated with a particular data storage system or a particular category of data.

Similar to virtual warehouse 502 discussed above, virtual warehouse 504 includes three execution nodes 526, 528, and 530. Execution node 526 includes a cache 532 and a processor 534. Execution node 528 includes a cache 536 and a processor 538. Execution node 530 includes a cache 540 and a processor 542. Additionally, virtual warehouse 506 includes three execution nodes 544, 546, and 548. Execution node 544 includes a cache 550 and a processor 552. Execution node 546 includes a cache 554 and a processor 556. Execution node 548 includes a cache 558 and a processor 560.

Although the execution nodes shown in FIG. 5 each include one cache and one processor, alternate embodiments may include execution nodes containing any number of processors and any number of caches. Additionally, the caches may vary in size among the different execution nodes. The caches shown in FIG. 5 store, in the local execution node, data that was retrieved from one or more data storage devices in a storage platform 314 (FIG. 3). Thus, the caches reduce or eliminate the bottleneck problems occurring in platforms that consistently retrieve data from remote storage systems. Instead of repeatedly accessing data from the remote storage devices, the systems and methods described herein access data from the caches in the execution nodes which is significantly faster and avoids the bottleneck problem discussed above. In some embodiments, the caches are implemented using high-speed memory devices that provide fast access to the cached data. Each cache can store data from any of the storage devices in storage platform 314.

Further, the cache resources and computing resources may vary between different execution nodes. For example, one execution node may contain significant computing resources and minimal cache resources, making the execution node useful for tasks that require significant computing resources. Another execution node may contain significant cache resources and minimal computing resources, making this execution node useful for tasks that require caching of large amounts of data. In some embodiments, the cache resources and computing resources associated with a particular execution node are determined when the execution node is created, based on the expected tasks to be performed by the execution node.

Additionally, the cache resources and computing resources associated with a particular execution node may change over time based on changing tasks performed by the execution node. For example, a particular execution node may be assigned more processing resources if the tasks performed by the execution node become more processor intensive. Similarly, an execution node may be assigned more cache resources if the tasks performed by the execution node require a larger cache capacity.

Although virtual warehouses 502-506 are associated with the same execution platform 312 of FIG. 3, the virtual warehouses may be implemented using multiple computing systems at multiple geographic locations. For example, virtual warehouse 502 can be implemented by a computing system at a first geographic location, while virtual warehouses 504 and 506 are implemented by another computing system at a second geographic location. In some embodiments, these different computing systems are cloud-based computing systems maintained by one or more different entities.

Additionally, each virtual warehouse is shown in FIG. 5 as having multiple execution nodes. The multiple execution nodes associated with each virtual warehouse may be implemented using multiple computing systems at multiple geographic locations. For example, a particular instance of virtual warehouse 502 implements execution nodes 508 and 510 on one computing platform at a particular geographic location, and implements execution node 512 at a different computing platform at another geographic location. Selecting particular computing systems to implement an execution node may depend on various factors, such as the level of resources needed for a particular execution node (e.g., processing resource requirements and cache requirements), the resources available at particular computing systems, communication capabilities of networks within a geographic location or between geographic locations, and which computing systems are already implementing other execution nodes in the virtual warehouse. Execution platform 312 is also fault tolerant. For example, if one virtual warehouse fails, that virtual warehouse is quickly replaced with a different virtual warehouse at a different geographic location.

A particular execution platform 312 may include any number of virtual warehouses 502-506. Additionally, the number of virtual warehouses in a particular execution platform is dynamic, such that new virtual warehouses are created when additional processing and/or caching resources are needed. Similarly, existing virtual warehouses may be deleted when the resources associated with the virtual warehouse are no longer necessary.

Figure 6:
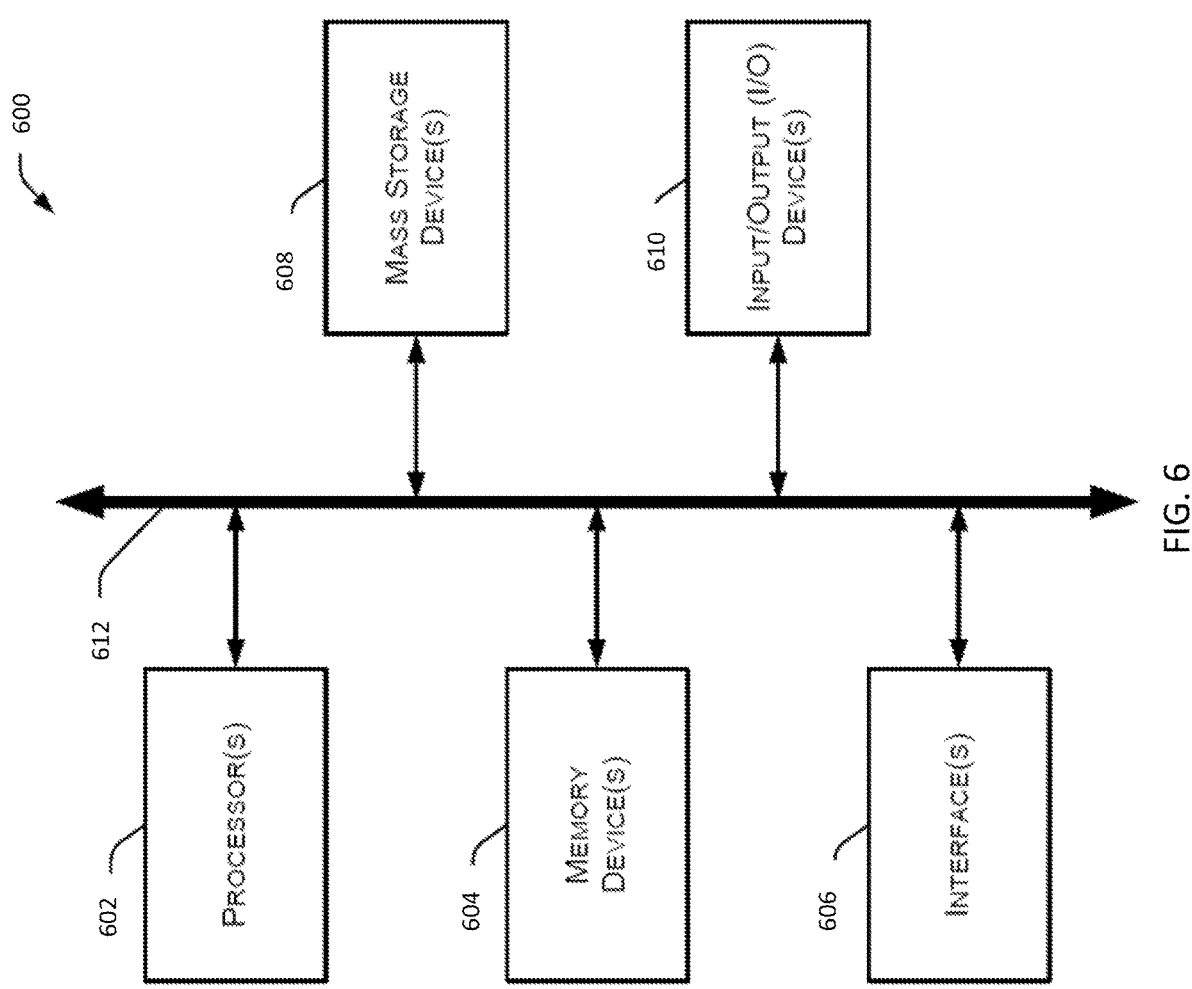
FIG. 6 illustrates a block diagram depicting an example computing device in accordance with the teachings of the disclosure.

FIG. 6 is a block diagram depicting an example computing device 600. In some embodiments, computing device 600 is used to implement one or more of the systems and components discussed herein. For example, computing device 600 may allow a user or administrator to access resource manager 302. Further, computing device 600 may interact with any of the systems and components described herein. Accordingly, computing device 600 may be used to perform various procedures and tasks, such as those discussed herein. Computing device 600 can function as a server, a client or any other computing entity. Computing device 600 can be any of a wide variety of computing devices, such as a desktop computer, a notebook computer, a server computer, a handheld computer, a tablet, and the like.

Computing device 600 includes one or more processor(s) 602, one or more memory device(s) 604, one or more interface(s) 606, one or more mass storage device(s) 608, and one or more Input/Output (I/O) device(s) 610, all of which are coupled to a bus 612. Processor(s) 602 include one or more processors or controllers that execute instructions stored in memory device(s) 604 and/or mass storage device(s) 608. Processor(s) 602 may also include various types of computer-readable media, such as cache memory.

Memory device(s) 604 include various computer-readable media, such as volatile memory (e.g., random access memory (RAM)) and/or nonvolatile memory (e.g., read-only memory (ROM)). Memory device(s) 604 may also include rewritable ROM, such as Flash memory.

Mass storage device(s) 608 include various computer readable media, such as magnetic tapes, magnetic disks, optical disks, solid state memory (e.g., Flash memory), and so forth. Various drives may also be included in mass storage device(s) 608 to enable reading from and/or writing to the various computer readable media. Mass storage device(s) 608 include removable media and/or non-removable media.

I/O device(s) 610 include various devices that allow data and/or other information to be input to or retrieved from computing device 600. Example I/O device(s) 610 include cursor control devices, keyboards, keypads, microphones, monitors or other display devices, speakers, printers, network interface cards, modems, lenses, CCDs or other image capture devices, and the like.

Interface(s) 606 include various interfaces that allow computing device 600 to interact with other systems, devices, or computing environments. Example interface(s) 606 include any number of different network interfaces, such as interfaces to local area networks (LANs), wide area networks (WANs), wireless networks, and the Internet.

Bus 612 allows processor(s) 602, memory device(s) 604, interface(s) 606, mass storage device(s) 608, and I/O device(s) 610 to communicate with one another, as well as other devices or components coupled to bus 612. Bus 612 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 600, and are executed by processor(s) 602. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Although the present disclosure is described in terms of certain preferred embodiments, other embodiments will be apparent to those of ordinary skill in the art, given the benefit of this disclosure, including embodiments that do not provide all of the benefits and features set forth herein, which are also within the scope of this disclosure. It is to be understood that other embodiments may be utilized, without departing from the scope of the present disclosure.

What is claimed is:

1. A non-transitory computer-readable medium storing instructions which, when executed by one or more third processors of a computing device, cause the computing device to:
   receive a query for information stored in one or more databases;
   access an execution plan comprising one or more steps on a set of data referenced by the query;
   initiate, within a first processor, a first parallel execution process in the execution plan to process the set of data and generate an intermediate result of a query;
   push, by the first processor, during execution of the query plan, the intermediate result to a plurality of second processors in the query plan for processing by the plurality of secondary parallel execution processes within the plurality of second processors, wherein each of the first processor and the plurality of second processors decoupled from a disk storage;
   initiate each of the plurality of secondary parallel execution processes with the plurality of second processors to process the intermediate result to generate a plurality of second results; and
   store a final result to disk storage within a storage platform.

2. The non-transitory computer-readable medium of claim 1, wherein the plurality of second results is generated without writing the intermediate result to disk storage.

3. The non-transitory computer-readable medium of claim 1, wherein each of the plurality of secondary parallel execution processes processes the intermediate result with a different operation.

4. The non-transitory computer-readable medium of claim 1, wherein the instructions further cause the computing device to:
   delay operation of at least one of the plurality of secondary parallel execution processes so as to coordinate timing among other secondary parallel execution processes of the plurality of secondary parallel execution processes.

5. The non-transitory computer-readable medium of claim 1, wherein the intermediate result comprises a plurality of rows of database data.

6. The non-transitory computer-readable medium of claim 1, wherein each of the plurality of secondary parallel execution processes are unique operators.

7. The non-transitory computer-readable medium of claim 1, wherein the intermediate result is not materialized.

8. The non-transitory computer-readable medium of claim 1, wherein the intermediate result generated by the first parallel execution processes is not materialized to a temporary structure.

9. The non-transitory computer-readable medium of claim 1, wherein the one or more databases are coupled to a database system that includes a relational database.

10. The non-transitory computer-readable medium of claim 9, wherein the relational database is a structured query language database.

11. The non-transitory computer-readable medium of claim 1, wherein the one or more databases are coupled to a database system is a multi-tenant database that isolates computing resources and data between different customers.

12. The non-transitory computer-readable medium of claim 1, wherein the each of first and the plurality of second processors is coupled to the disk storage via a communications network.

13. The non-transitory computer-readable medium of claim 1, wherein the each of the first and the second plurality of processors includes a local cache.

14. A method comprising:
receiving a query for information stored in one or more databases;
accessing an execution plan comprising one or more steps on a set of data referenced by the query;
initiating, within a first processor, a first parallel execution process in the execution plan to process the set of data and generate an intermediate result of a query;
pushing, by the first processor, during execution of the query plan, the intermediate result to a plurality of second processors in the query plan for processing by the plurality of secondary parallel execution processes within the plurality of second processors, wherein each of the first processor and the plurality of second processors decoupled from a disk storage;
initiating each of the plurality of secondary parallel execution processes with the plurality of second processors to process the intermediate result to generate a plurality of second results; and
storing a final result to disk storage within a storage platform.

15. The method of claim 14, wherein the plurality of second results generated without writing the intermediate result to disk storage.

16. The method of claim 14, wherein each of the plurality of secondary parallel execution processes process the intermediate result with a different operation.

17. The method of claim 14, further comprising:
delaying operation of at least one of the plurality of secondary parallel execution processes so as to coordinate timing among other secondary parallel execution processes of the plurality of secondary parallel execution processes.

18. The method of claim 14, wherein the intermediate result comprises a plurality of rows of database data.

19. The method of claim 14, wherein each of the plurality of secondary parallel execution processes are unique operators.

20. The method of claim 14, wherein the intermediate result is not materialized.

21. The method of claim 14, wherein the intermediate result generated by the first parallel execution processes is not materialized to a temporary structure.

22. The method of claim 14, wherein the set of data is stored in a relational database.

23. The method of claim 22, wherein the relational database is a structured query language database.

24. The method of claim 14, wherein the database system is a multi-tenant database that isolates computing resources and data between different customers.

25. The method of claim 14, wherein the each of the first and the second plurality of processors is coupled to the disk storage via a communications network.

26. The method of claim 14, wherein the each of the first and the second plurality of processors includes a local cache.

27. A system comprising:
a query coordinating process programmed to:
receive a query for information stored in one or more databases, and
access an execution plan comprising one or more steps on a set of data referenced by the query;
a first processor programmed to:
initiate a first parallel execution process in the execution plan to process the set of data and generate an intermediate result of a query, and
push, by the one or more processors, during execution of the query plan, the intermediate result to a plurality of secondary processors in the query plan for concurrent processing by the plurality of secondary processors, wherein each of the first processor and the plurality of second processors decoupled from a disk storage; and
the one or more second processors programmed to initiate each of the plurality of secondary parallel execution processes to process the intermediate result to generate a plurality of second results; and
a storage platform programmed to store a final result to disk storage.

28. The system of claim 27, wherein the plurality of second results is generated without writing the intermediate result to the disk storage.

29. The system of claim 27, wherein each of the plurality of secondary parallel execution processes process the intermediate result with a different operation.

30. The system of claim 27, wherein the query coordinating process further to:
delay operation of at least one of the plurality of secondary parallel execution processes so as to coordinate timing among other secondary parallel execution processes of the plurality of secondary parallel execution processes.

* * * * *

UNITED STATES PATENT AND TRADEMARK OFFICE
CERTIFICATE OF CORRECTION

| | |
|---|---|
| PATENT NO. | : 10,795,914 B2 |
| APPLICATION NO. | : 16/862458 |
| DATED | : October 6, 2020 |
| INVENTOR(S) | : Cruanes et al. |

It is certified that error appears in the above-identified patent and that said Letters Patent is hereby corrected as shown below:

In the Claims

In Claim 1, Column 12, Lines 13 and 15, please change "query" to --execution--; and Line 24, please change "to disk" to --to the disk--.

In Claim 11, Column 12, Line 62, please change "system is" to --system that is--.

In Claim 14, Column 13, Line 11, please change "a" to --the--; Lines 13 and 14, please change "query plan" to --execution plan--; and Line 13, please change "to disk" to --to the disk--.

In Claim 15, Column 13, Line 26, please change "results generated" to --results is generated--.

In Claim 27, Column 14, Line 20, please change "a" to --the--; Lines 22 and 23, change "query plan" to --execution plan--; and Lines 32-33, change "to disk" to --to the disk--.

Signed and Sealed this
Third Day of May, 2022

Katherine Kelly Vidal
*Director of the United States Patent and Trademark Office*